US009107734B2

(12) United States Patent
Belson (10) Patent No.: US 9,107,734 B2
(45) Date of Patent: Aug. 18, 2015

(54) EMBOLIC PROTECTION DEVICE

(75) Inventor: Amir Belson, Los Altos, CA (US)

(73) Assignee: EMBOLINE, INC., Los Altos, CA (US)

( * ) Notice: Subject to any disclaimer, the term of this patent is extended or adjusted under 35 U.S.C. 154(b) by 755 days.

(21) Appl. No.: 12/532,630

(22) PCT Filed: Nov. 29, 2007

(86) PCT No.: PCT/US2007/024558
§ 371 (c)(1),
(2), (4) Date: Apr. 26, 2010

(87) PCT Pub. No.: WO2008/066881
PCT Pub. Date: Jun. 5, 2008

(65) Prior Publication Data
US 2010/0312268 A1      Dec. 9, 2010

Related U.S. Application Data

(60) Provisional application No. 60/861,687, filed on Nov. 29, 2006.

(51) Int. Cl.
*A61F 2/01*          (2006.01)

(52) U.S. Cl.
CPC ............. *A61F 2/01* (2013.01); *A61F 2002/011* (2013.01); *A61F 2002/018* (2013.01); *A61F 2230/0006* (2013.01); *A61F 2230/0067* (2013.01); *A61F 2230/0069* (2013.01)

(58) Field of Classification Search
CPC ..................................................... A61F 2/013
USPC ............ 606/108; 623/23.67, 23.7, 1.11, 1.12, 623/1.13, 1.24, 1.26, 1.23
See application file for complete search history.

(56) References Cited

U.S. PATENT DOCUMENTS 4,723,549 A    2/1988  Wholey et al.
4,790,809 A   12/1988  Kuntz
(Continued)

FOREIGN PATENT DOCUMENTS

WO    WO 03/094791 A2    11/2003
WO    WO 2004/019817 A1   3/2004

OTHER PUBLICATIONS

U.S. Appl. No. 13/343,538, filed Jan. 4, 2012, Belson.
(Continued)

*Primary Examiner* — Katherine Dowe
*Assistant Examiner* — Richard Louis
(74) *Attorney, Agent, or Firm* — Wilson Sonsini Goodrich & Rosati (57) ABSTRACT

An embolic protection device for use in a patient's blood vessel, such as the aorta, has an approximately cylindrical outer structure made of a filter mesh material and an approximately conical inner structure also made of a filter mesh material. On the downstream end of the embolic protection device, the wider end of the conical inner structure is joined to the cylindrical outer structure. The upstream end of the embolic protection device is open for blood to flow between the conical inner structure and the cylindrical outer structure. The space between the conical inner structure and the cylindrical outer structure defines a collection chamber for captured emboli. The narrow upstream end of the conical inner structure has a catheter port with a resilient seal that is sized for passage of a catheter shaft. The filter mesh material may be self-supporting or it may be supported on a resilient-framework or an inflatable framework.

32 Claims, 7 Drawing Sheets

(56) References Cited

U.S. PATENT DOCUMENTS

| | | | |
|---|---|---|---|
| 5,108,419 A | 4/1992 | Reger et al. | |
| 5,197,485 A * | 3/1993 | Grooters | 600/571 |
| 5,769,816 A * | 6/1998 | Barbut et al. | 604/93.01 |
| 5,769,819 A | 6/1998 | Schwab et al. | |
| 5,797,880 A * | 8/1998 | Erskine | 604/110 |
| 5,800,525 A | 9/1998 | Bachinski et al. | |
| 6,013,051 A * | 1/2000 | Nelson | 604/93.01 |
| 6,117,154 A | 9/2000 | Barbut et al. | |
| 6,139,517 A | 10/2000 | Macoviak et al. | |
| 6,152,144 A | 11/2000 | Lesh et al. | |
| 6,254,563 B1 | 7/2001 | Macoviak et al. | |
| 6,258,120 B1 * | 7/2001 | McKenzie et al. | 623/1.36 |
| 6,348,063 B1 | 2/2002 | Yassour et al. | |
| 6,355,051 B1 * | 3/2002 | Sisskind et al. | 606/200 |
| 6,361,545 B1 * | 3/2002 | Macoviak et al. | 606/200 |
| 6,371,935 B1 | 4/2002 | Macoviak et al. | |
| 6,461,370 B1 | 10/2002 | Gray et al. | |
| 6,499,487 B1 * | 12/2002 | McKenzie et al. | 128/898 |
| 6,537,297 B2 | 3/2003 | Tsugita et al. | |
| 6,682,543 B2 * | 1/2004 | Barbut et al. | 606/159 |
| 6,695,864 B2 | 2/2004 | Macoviak et al. | |
| 6,746,469 B2 | 6/2004 | Mouw | |
| 6,808,520 B1 * | 10/2004 | Fourkas et al. | 604/526 |
| 7,232,453 B2 | 6/2007 | Shimon | |
| 7,235,060 B2 * | 6/2007 | Kraus | 604/9 |
| 7,758,606 B2 | 7/2010 | Streeter et al. | |
| 7,766,932 B2 * | 8/2010 | Melzer et al. | 606/200 |
| 8,114,114 B2 | 2/2012 | Belson | |
| 8,308,754 B2 | 11/2012 | Belson | |
| 8,414,482 B2 | 4/2013 | Belson | |
| 8,430,904 B2 | 4/2013 | Belson | |
| 8,679,149 B2 | 3/2014 | Belson | |
| 8,728,114 B2 | 5/2014 | Belson | |
| 2001/0044632 A1 * | 11/2001 | Daniel et al. | 606/200 |
| 2002/0004667 A1 * | 1/2002 | Adams et al. | 606/200 |
| 2002/0058964 A1 * | 5/2002 | Addis | 606/200 |
| 2002/0128680 A1 * | 9/2002 | Pavlovic | 606/200 |
| 2003/0040736 A1 * | 2/2003 | Stevens et al. | 604/532 |
| 2003/0100940 A1 | 5/2003 | Yodfat | |
| 2004/0034380 A1 * | 2/2004 | Woolfson et al. | 606/170 |
| 2004/0073253 A1 * | 4/2004 | Morrill et al. | 606/200 |
| 2004/0138692 A1 | 7/2004 | Phung et al. | |
| 2004/0215167 A1 * | 10/2004 | Belson | 604/526 |
| 2004/0225354 A1 * | 11/2004 | Allen et al. | 623/2.11 |
| 2005/0010246 A1 * | 1/2005 | Streeter et al. | 606/200 |
| 2005/0283186 A1 * | 12/2005 | Berrada et al. | 606/200 |
| 2006/0287668 A1 * | 12/2006 | Fawzi et al. | 606/200 |
| 2006/0293706 A1 * | 12/2006 | Shimon | 606/200 |
| 2007/0027534 A1 * | 2/2007 | Bergheim et al. | 623/2.11 |
| 2007/0060944 A1 * | 3/2007 | Boldenow et al. | 606/200 |
| 2007/0073246 A1 * | 3/2007 | Simon | 604/246 |
| 2008/0027481 A1 * | 1/2008 | Gilson et al. | 606/200 |
| 2009/0149881 A1 | 6/2009 | Vale et al. | |
| 2010/0274277 A1 | 10/2010 | Eaton | |
| 2014/0058372 A1 | 2/2014 | Belson | |
| 2014/0155929 A1 | 6/2014 | Belson | |

OTHER PUBLICATIONS

International search report and written opinion dated Apr. 9, 2008 for PCT/US2007/024558.
International search report dated Jan. 15, 2004 for PCT/US2003/026938.
U.S. Appl. No. 13/347,046, filed Jan. 10, 2012, Belson.
U.S. Appl. No. 13/735,864, filed Jan. 7, 2013, Russell et al.
Notice of allowance dated Aug. 10, 2012 for U.S. Appl. No. 13/347,046.
Office action dated Jan. 17, 2013 for U.S. Appl. No. 13/648,992.
Office action dated Feb. 11, 2009 for U.S. Appl. No. 10/493,854.
Office action dated Feb. 26, 2008 for U.S. Appl. No. 10/493,854.
Office action dated Apr. 10, 2012 for U.S. Appl. No. 13/343,538.
Office action dated Jul. 12, 2011 for U.S. Appl. No. 10/493,854.
Office action dated Aug. 20, 2010 for U.S. Appl. No. 10/493,854.
Office action dated Sep. 14, 2011 for U.S. Appl. No. 10/493,854.
Office action dated Dec. 11, 2012 for U.S. Appl. No. 13/343,538.
U.S. Appl. No. 13/866,887, filed Apr. 19, 2013, Belson.
International search report and written opinion dated Apr. 22, 2013 for PCT Application No. US2013/20563.
Notice of allowance dated Feb. 26, 2013 for U.S. Appl. No. 13/648,986.
Notice of allowance dated Mar. 1, 2013 for U.S. Appl. No. 13/343,538.
Office action dated Mar. 13, 2013 for U.S. Appl. No. 12/532,630.
Office action dated Apr. 10, 2013 for U.S. Appl. No. 12/532,630.
Office action dated Jul. 17, 2013 for U.S. Appl. No. 13/735,864.
Office action dated Jul. 23, 2013 for U.S. Appl. No. 13/648,992.
Office action dated Jul. 23, 2013 for U.S. Appl. No. 13/866,887.
Office action dated Jan. 24, 2014 for U.S. Appl. No. 13/735,864.
U.S. Appl. No. 14/537,814, filed Nov. 10, 2014, Russell et al.
Notice of Allowance dated Nov. 1, 2013 for U.S. Appl. No. 13/648,992.
Notice of Allowance dated Nov. 18, 2013 for U.S. Appl. No. 13/866,887.
Notice of Allowance dated Nov. 23, 2011 for U.S. Appl. No. 10/493,854.
US 6,348,062, 02/2002, Hopkins et al. (withdrawn)

* cited by examiner

EMBOLIC PROTECTION DEVICE

CROSS REFERENCE TO OTHER APPLICATIONS

The present application claims the benefit of U.S. Provisional Application 60/861,687, filed on Nov. 29, 2006, the disclosure of which is incorporated by reference.

FIELD OF THE INVENTION

The present invention relates to apparatus and methods for providing embolic protection in a patient's vascular system. In particular, it relates to an embolic protection device that can be deployed in a patient's aorta to protect the aortic arch vessels and downstream organs from potential emboli. The embolic protection device can be used acutely, for example for embolic protection during cardiac surgery and interventional cardiology procedures, or it can be implanted for chronic embolic protection, for example from cardiogenic emboli or emboli from ruptured or vulnerable aortic plaque.

BACKGROUND OF THE INVENTION

Cerebral embolism is a known complication of cardiac surgery, cardiopulmonary bypass and catheter-based interventional cardiology and electrophysiology procedures. Embolic particles, which may include thrombus, atheroma and lipids, may become dislodged by surgical or catheter manipulations and enter the bloodstream, embolizing in the brain or other vital organs downstream. Other sources of potential emboli include cardiogenic emboli, such as thrombus that results from chronic atrial fibrillation, and emboli from ruptured or vulnerable aortic plaque. Cerebral embolism can lead to neuropsychological deficits, stroke and even death. Other organs downstream can also be damaged by embolism, resulting in diminished function or organ failure. Prevention of embolism would benefit patients and improve the outcome of these procedures.

Given that the sources of potential emboli can be acute or chronic, it would be advantageous to provide an embolic protection device that can either be used acutely, for example for embolic protection during cardiac surgery and interventional cardiology procedures, or that can be implanted for chronic embolic protection, for example from cardiogenic emboli or emboli from ruptured or vulnerable aortic plaque. A further advantage would be realized by providing an embolic protection device that can be implanted without interfering with transluminal aortic access for performing future surgeries and other interventional or diagnostic procedures. Another advantage would come from providing an embolic protection device that can be retrieved and removed from the patient after the necessity for it has passed. Yet another advantage would come from providing an embolic protection device that can be deployed and retrieved using minimally invasive techniques.

Previous devices for preventing cerebral embolism are described in the following patents and patent applications, which are hereby incorporated by reference: U.S. Pat. App. 20040215167 Embolic protection device, PCT App. WO/2004/019817 Embolic protection device, U.S. Pat. No. 6,371,935 Aortic catheter with flow divider and methods for preventing cerebral embolization, U.S. Pat. No. 6,361,545 Perfusion filter catheter, U.S. Pat. No. 6,254,563 Perfusion shunt apparatus and method, U.S. Pat. No. 6,139,517 Perfusion shunt apparatus and method, U.S. Pat. No. 6,537,297 Methods of protecting a patient from embolization during surgery, U.S. Pat. No. 6,499,487 Implantable cerebral protection device and methods of use, U.S. Pat. No. 5,769,816 Cannula with associated filter, U.S. Pat. App. 20030100940 Implantable intraluminal protector device and method of using same for stabilizing atheromas.

DESCRIPTION OF THE INVENTION

Figure 1:
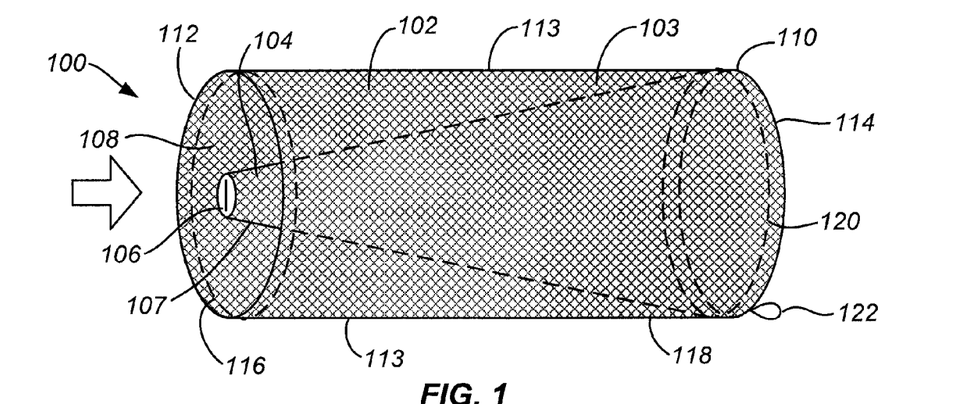
FIG. 1 shows an embolic protection device according to the present invention in an expanded or deployed condition.

FIG. 1 shows an embolic protection device 100 according to the present invention in an expanded or deployed condition. The embolic protection device 100 has an approximately cylindrical outer structure 102 made of a filter mesh material and an approximately conical inner structure 104 also made of a filter mesh material. On the downstream end 110 of the embolic protection device 100, the wider end of the conical inner structure 104 is joined to the cylindrical outer structure 102. The upstream end 108 of the embolic protection device 100 is open for blood to flow between the conical inner structure 104 and the cylindrical outer structure 102 as indicated by the arrow in FIG. 1. The space between the conical inner structure 104 and the cylindrical outer structure 102 defines a collection chamber 103 for captured emboli.

The filter mesh material of the conical inner structure 104 and the cylindrical outer structure 102 may be made of knitted, woven or nonwoven fibers, filaments or wires and will have a pore size chosen to stop emboli above a certain size to pass through. The filter mesh material may be made of a metal, a polymer or a combination thereof and may optionally have an antithrombogenic coating on its surface. The filter mesh material of the conical inner structure 104 and the cylindrical outer structure 102 may have the same pore size or they may have different pore sizes. For example, the filter mesh material of the conical inner structure 104 and the cylindrical outer structure 102 may both have a pore size in the range of approximately 1 mm to 0.1 mm or even smaller, depending on whether it is intended to capture macroemboli only or microemboli as well. Alternatively, the filter mesh material of the cylindrical outer structure 102 may have a pore size to stop microemboli as small as 0.1 mm and the filter mesh material of the conical inner structure 104 may have a pore size to stop macroemboli larger than 1 mm. In another alternate embodiment, a portion of the cylindrical outer structure 102 configured to be positioned away from the aortic arch vessels may be constructed of an impermeable material rather than the filter mesh material.

The narrow upstream end of the conical inner structure 104 has a catheter port 106 with a resilient seal that is sized for passage of a catheter shaft.

Figure 2:
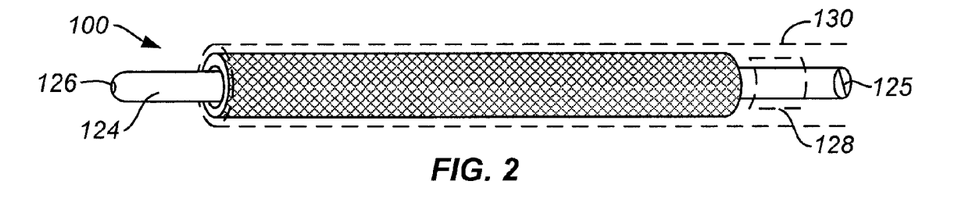
FIG. 2 shows the embolic protection device of FIG. 1 in an undeployed or retracted condition.

FIG. 2 shows the embolic protection device 100 of FIG. 1 in an undeployed or retracted condition. A delivery catheter 124 is inserted through the catheter port 106 of the embolic protection device 100. Typically, the delivery catheter 124 will be constructed with an internal lumen 125 that terminates in a guidewire port 126 at the distal end of the catheter 124. Optionally, a tubular outer delivery sheath 130 may be used to maintain the embolic protection device 100 in the undeployed condition. The delivery catheter 124 may optionally include a shoulder 128 positioned proximal to the embolic protection device 100 to maintain the position of the embolic protection device 100 on the delivery catheter 124 as the delivery sheath 130 is withdrawn during deployment. Alternatively, a pusher catheter (not shown) that fits in between the delivery catheter 124 and the delivery sheath 130 may be used to facilitate deployment.

Optionally, when the embolic protection device 100 is intended to be used for embolic protection during a catheter-based diagnostic or interventional procedure, the delivery catheter 124 may be configured as a diagnostic catheter, a guiding catheter or therapeutic catheter.

Figure 13:
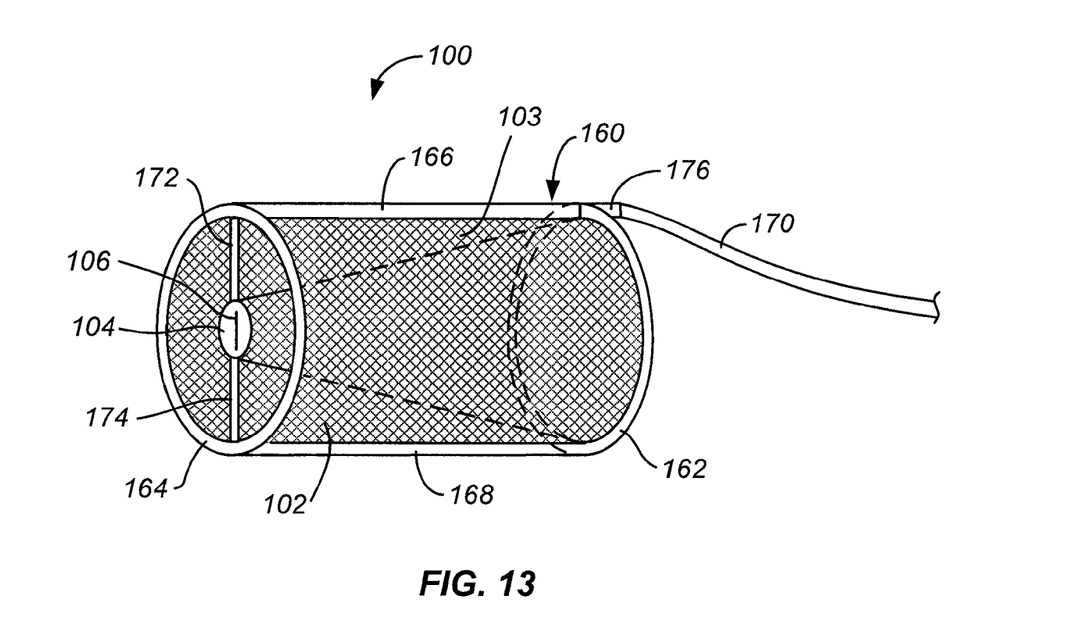
FIG. 13 shows the embolic protection device of FIG. 12 in an inflated condition.

The embolic protection device 100 will preferably be self-supporting in the deployed condition. This can be accomplished with a variety of different constructions. In one example, the conical inner structure 104 and the cylindrical outer structure 102 can be constructed with a resilient filter mesh material that can be compressed into the undeployed condition and will self-expand into the deployed condition. Alternatively, the filter mesh can be supported by a framework that includes an upstream hoop 112, a downstream hoop 114 and one or more longitudinal struts 113 that form the cylindrical outer structure 102 and one or more angled struts 107 that, together with the downstream hoop 114, form the conical inner structure 104. In an alternate construction, the upstream end of the conical inner structure 104 can be supported by one or more radial struts connected to the upstream hoop 112, obviating the need for the angled struts 107. (FIG. 13 shows an example of a framework that uses radial struts 172, 174 to support the conical inner structure 104.) The hoops and struts may be made of a resilient metal and/or polymer material to make a self-expanding framework or a malleable or plastically deformable material to make a framework that can be expanded with an inflatable balloon or other expansion mechanism (not shown). Alternatively, the framework can be made of a shape-memory material that can be used to deploy and/or retract the embolic protection device 100. The filter mesh supported on the framework can be resilient, flaccid or plastically deformable. Hybrid constructions that combine features of the self-supporting structure and the frame-supported structure may also be used. Hybrid deployment methods, such as balloon-assisted self-expansion can also be utilized.

The embolic protection device 100 may be constructed with the conical inner structure 104 and the cylindrical outer structure 102 having approximately the same longitudinal dimensions, as shown in the drawings. Alternatively, the conical inner structure 104 or the cylindrical outer structure 102 can be made longer or shorter without adversely affecting the performance of the product. In another alternate construction, the cylindrical outer structure 102 can be made slightly conical with the larger end of the cone on the upstream side.

Optionally, the embolic protection device 100 may include features to assist in retracting the device for retrieval from the patient's aorta. For example, the upstream end 108 and the downstream end 110 of the embolic protection device 100 may be constructed with retraction members 116, 120 that are configured like purse strings or lassos around the circumference of the cylindrical outer structure 102. A pull loop 122 or other graspable structure near the downstream end 110 of the embolic protection device 100 is connected to the retraction members 116, 120 by one or more connecting members 113. Optionally, two separate pull loops 122 may be provided for selectively retracting the upstream and downstream retraction members 116, 120. The retraction members 116, 120 and connecting members 113 may be made of suture, wire, plastic filament or a combination of these materials. In an alternate construction, the support hoops 112, 114 described above may also be configured to serve as the retraction members 116, 120.

Figure 3:
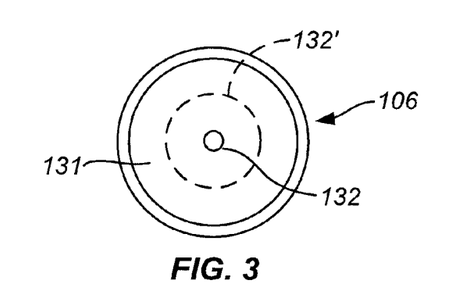
FIG. 3 shows an enlarged view of a catheter port for use in the embolic protection device of FIG. 1.

FIG. 3 shows an enlarged view of a catheter port 106 for use in the embolic protection device 100. The catheter port 106 is located at the narrow upstream end of the conical inner structure 104, as shown in FIG. 1. The catheter port 106 has a resilient seal that is sized for passage of a catheter shaft. The resilient seal of the catheter port 106 does not need to make a perfect hemostatic seal when the catheter port 106 is empty or when there is a catheter or guidewire through the catheter port 106; the only requirement is that it should exclude the passage of emboli above a certain size. In this embodiment, the resilient seal is in the form of an elastomeric disk or ring 131 with a hole 132 through the center that can stretch 132' to accommodate a range of catheter sizes. The elastomeric disk 131 will preferably have a low coefficient of friction and/or a lubricious coating so that movement of a catheter through the catheter port 106 will not jostle or dislodge the embolic protection device 100.

Figure 4:
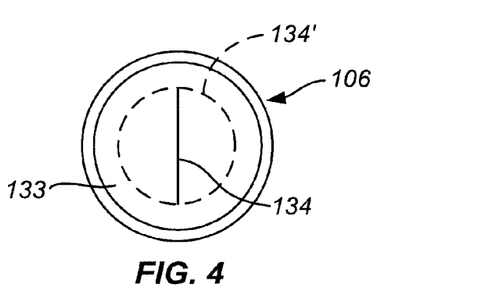
FIG. 4 shows another embodiment of a catheter port for use in the embolic protection device of FIG. 1.

FIG. 4 shows another embodiment of a catheter port 106 for use in the embolic protection device 100 of FIG. 1. In this embodiment, the resilient seal is in the form of an elastomeric disk 133 with a slit 134 through the center that can stretch 134' to accommodate a range of catheter sizes. The elastomeric disk 133 will preferably have a low coefficient of friction and/or a lubricious coating so that movement of a catheter through the catheter port 106 will not jostle or dislodge the embolic protection device 100.

Figure 5:
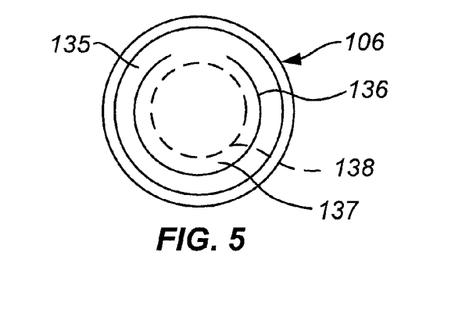
FIG. 5 shows another embodiment of a catheter port for use in the embolic protection device of FIG. 1.

FIG. 5 shows another embodiment of a catheter port 106 for use in the embolic protection device 100 of FIG. 1. In this embodiment, the resilient seal is in the form of an elastomeric disk 135 with a flap or trap door 136 through the center that can open by bending in the upstream direction to allow passage of a catheter. Optionally, the resilient seal may also include a second elastomeric disk 137 on the downstream side with a hole 138 through it slightly smaller than the trap door 136 that will provide a sliding seal around a catheter shaft and will support the flap or trap door 136 against blood pressure while it is in the closed position. The elastomeric disks 135, 137 will preferably have a low coefficient of friction and/or a lubricious coating so that movement of a catheter through the catheter port 106 will not jostle or dislodge the embolic protection device 100.

Figure 6:
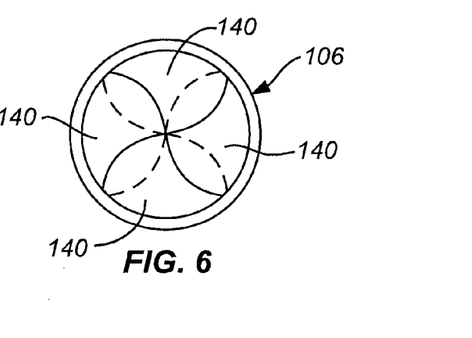
FIG. 6 shows another embodiment of a catheter port for use in the embolic protection device of FIG. 1.

FIG. 6 shows another embodiment of a catheter port 106 for use in the embolic protection device 100 of FIG. 1. In this embodiment, the resilient seal is in the form of a plurality of resilient flaps 140 that overlap or interdigitate to form a seal, but that can bend back to allow passage of a catheter. The example shown has four approximately semicircular flaps 140 that overlap one another to form a seal. Other numbers and geometries of flaps are also possible. The resilient flaps 140 will preferably have a low coefficient of friction and/or a lubricious coating so that movement of a catheter through the catheter port 106 will not jostle or dislodge the embolic protection device 100.

Figure 7:
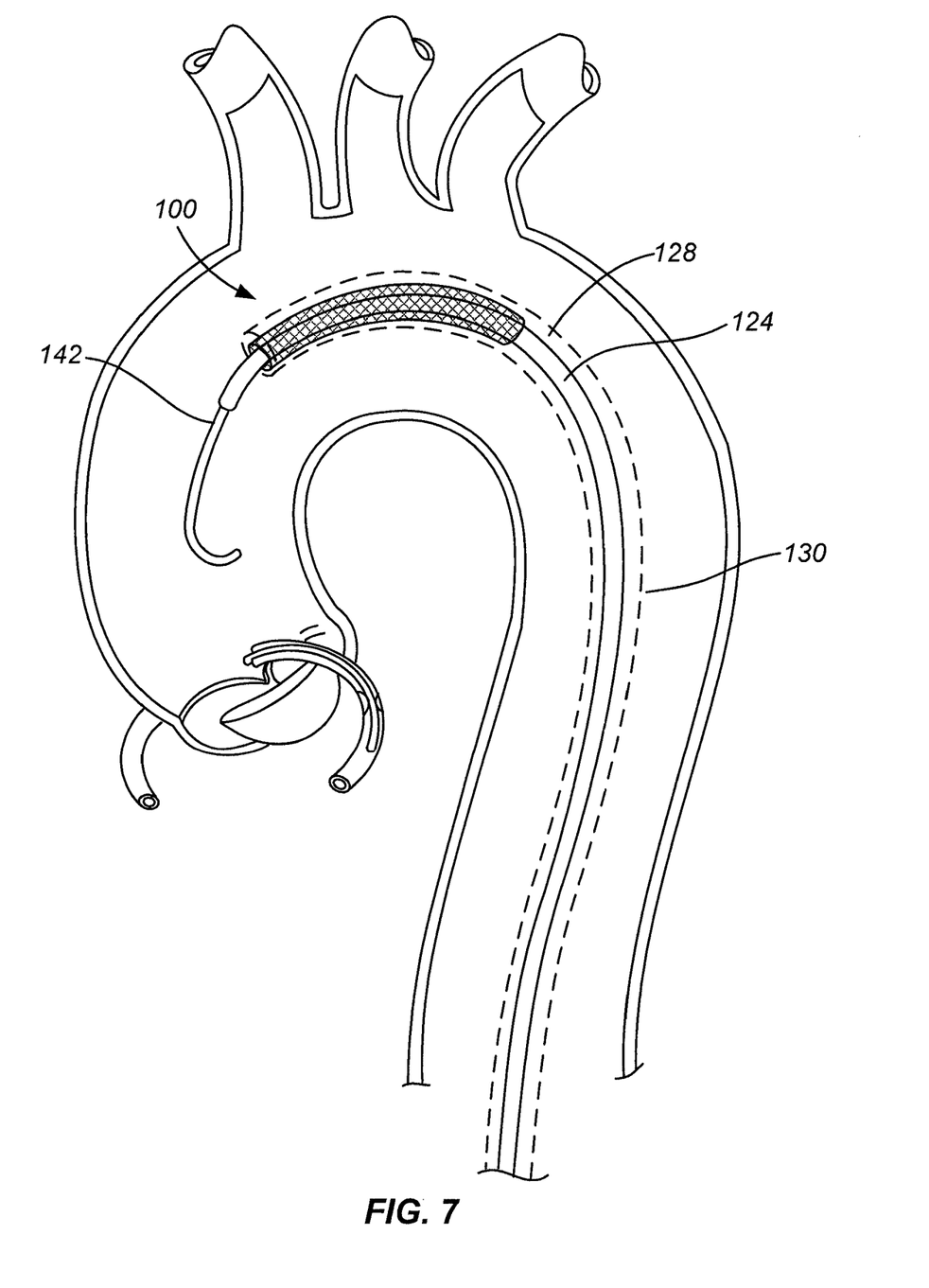
FIG. 7 shows an embolic protection device in an undeployed condition being inserted into a patient's aortic arch.

FIG. 7 shows an embolic protection device 100 in an undeployed condition mounted on a delivery catheter 126 being inserted over a guidewire 142 into a patient's aortic arch. Optionally, a delivery sheath 130 may be used to hold the embolic protection device 100 in the undeployed position. Once the embolic protection device 100 is at the desired location, the embolic protection device 100 is deployed, for example by withdrawing the delivery sheath 130 and allowing the embolic protection device 100 to expand. If the delivery catheter 126 is in the form of a diagnostic or therapeutic catheter, the catheter 126 can be advanced after the embolic protection device 100 is deployed to perform a diagnostic or interventional procedure. Optionally, the embolic protection device 100 can be retracted and withdrawn with the delivery catheter 126 after the diagnostic or interventional procedure has been completed. Alternatively, the delivery catheter 126 can be withdrawn, leaving the embolic protection device 100 in place.

Figure 8:
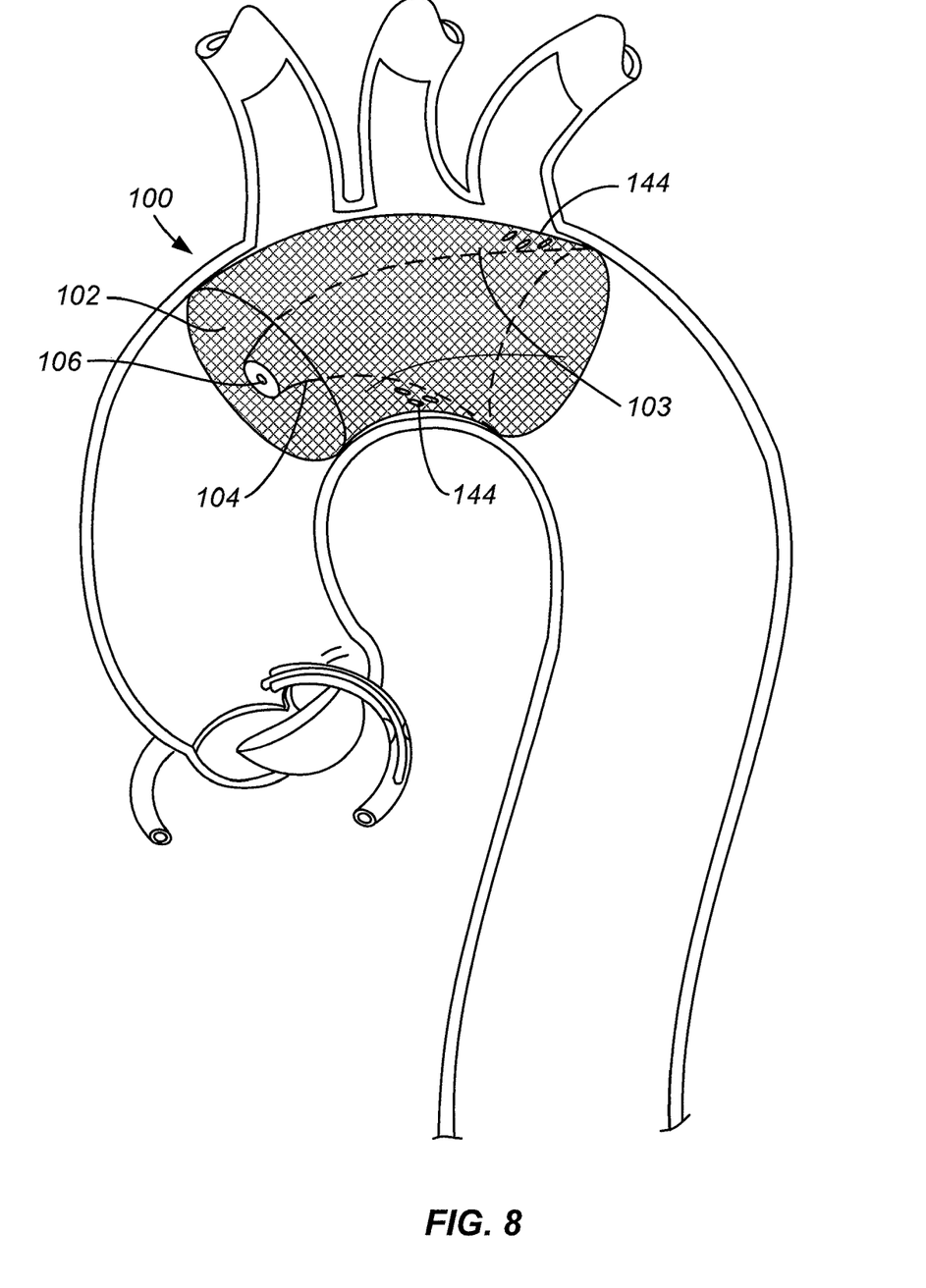
FIG. 8 shows the embolic protection device implanted in a patient's aortic arch.

FIG. 8 shows the embolic protection device 100 implanted in a patient's aortic arch with the delivery catheter 126 completely withdrawn. The upstream end of the embolic protection device 100 is preferably located upstream of the aortic arch vessels and downstream end of the embolic protection device 100 is preferably located downstream of the aortic arch vessels, as shown. Alternatively, the entire embolic protection device 100 can be located in the ascending aorta upstream of the aortic arch vessels. Potential emboli 144 are captured in the collection chamber 103 between the conical inner structure 104 and the cylindrical outer structure 102.

Figure 9:
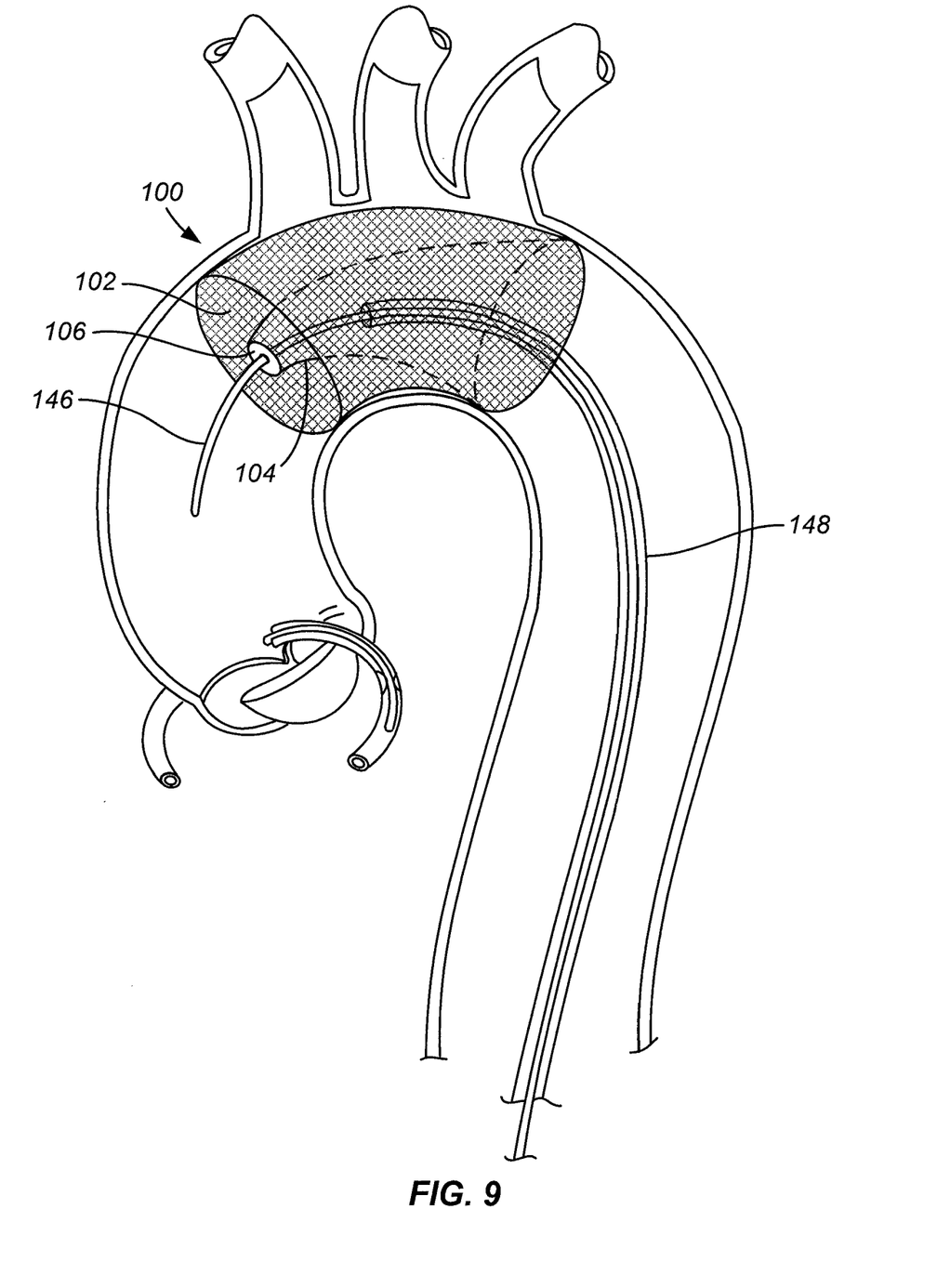
FIG. 9 shows a guidewire passing through the catheter port of an implanted embolic protection device.

The catheter port 106 in the embolic protection device 100 allows transluminal aortic access for performing future surgeries and other interventional or diagnostic procedures. FIG. 9 shows a guidewire 146 passing through the catheter port 106 to guide a diagnostic or therapeutic catheter 148 through an implanted embolic protection device 100. The conical inner structure 104 assists by funneling the guidewire 146 into the catheter port 106. The catheter 148 is then advanced through the catheter port 106 over the guidewire 146.

Figure 10:
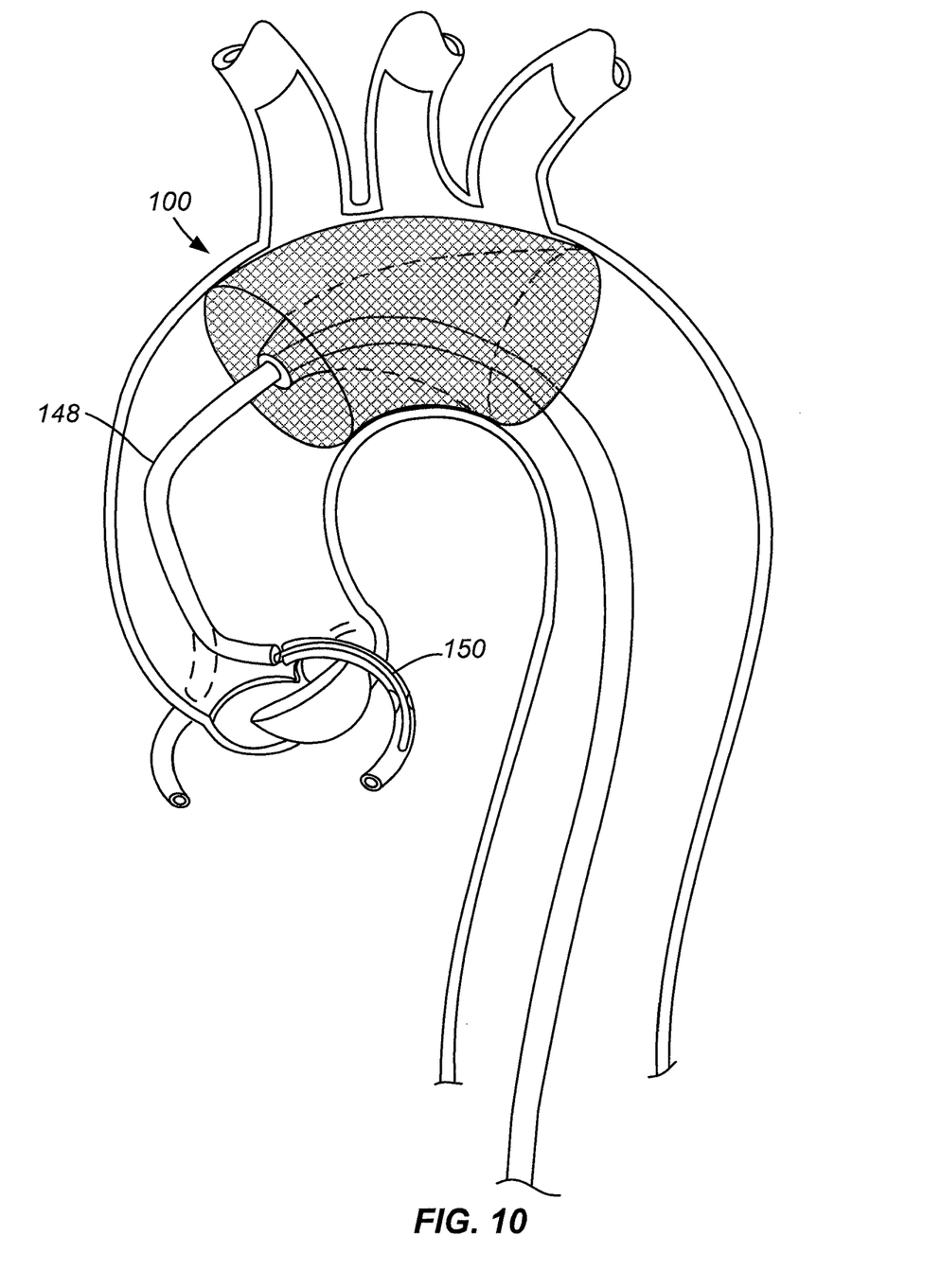
FIG. 10 shows a catheter-based interventional procedure being performed with the implanted embolic protection device in place.

FIG. 10 shows a catheter-based interventional procedure being performed with the implanted embolic protection device 100 in place. In this example, a coronary guiding catheter 148 has been advanced through the catheter port 106 of the embolic protection device 100 to selectively catheterize one of the coronary arteries. A therapeutic catheter 150 has been advanced through the guiding catheter 148 for performing a coronary intervention.

Figure 11:
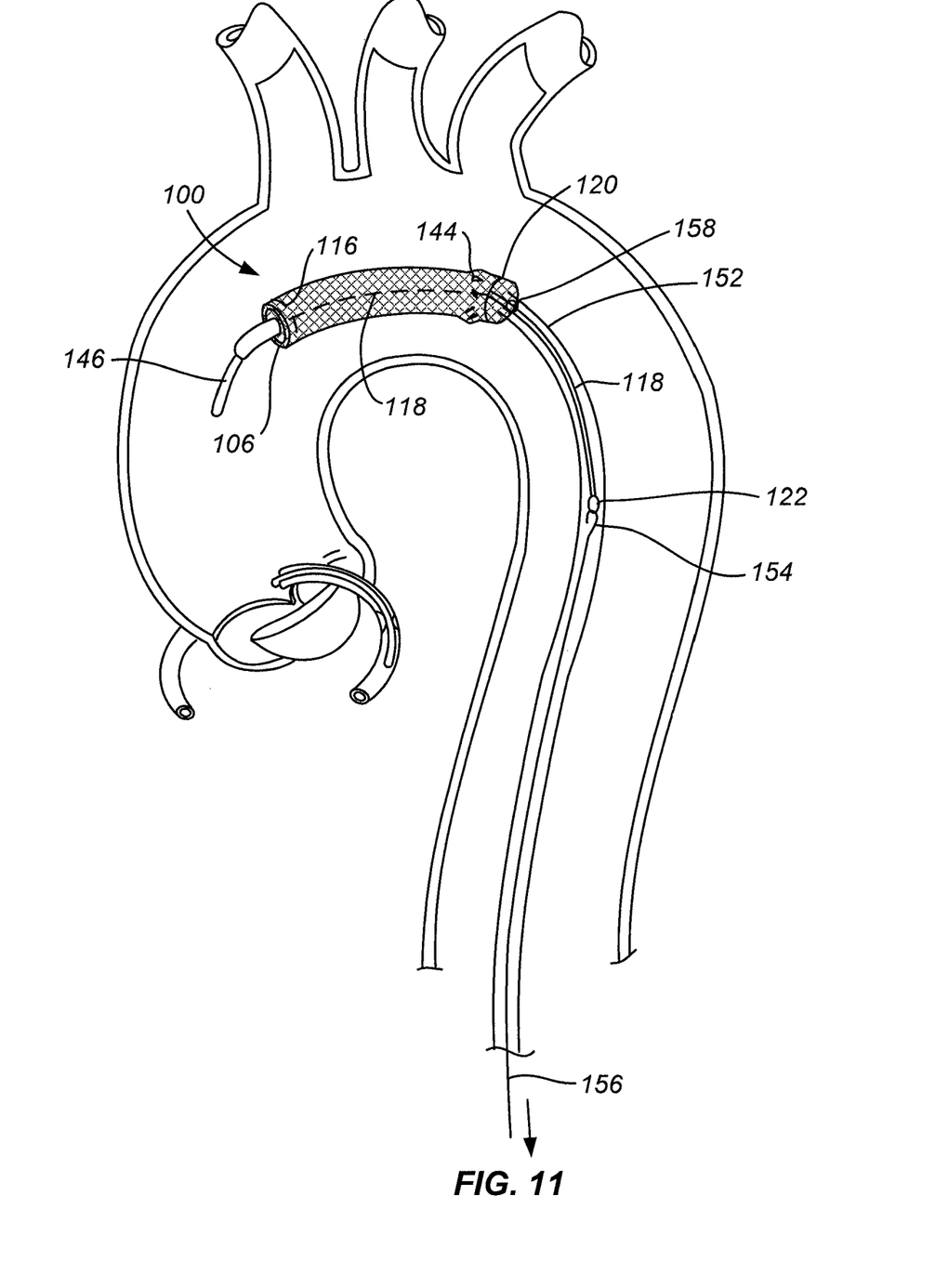
FIG. 11 shows an embolic protection device in a retracted condition for removal from the patient's aorta.

FIG. 11 shows an embolic protection device 100 in a retracted condition for removal from the patient's aorta. A retrieval catheter 152 has been inserted intraluminally over a guidewire 146 to the location of the embolic protection device 100. Optionally, the guidewire 146 and retrieval catheter 152 may be inserted into the conical inner structure 104 and/or through the catheter port 106. A hook 154 on the distal end of an elongated member 156 within the retrieval catheter 152 has engaged the pull loop 122 on the embolic protection device 100. The hook 154 may engage the pull loop 122 through a distal port or a side port 158 on the retrieval catheter 152. The hook 154 and the pull loop 122 are withdrawn into the retrieval catheter 152, pulling on the connecting member 118 and causing the retraction members 116, 120 to tighten and collapse the embolic protection device 100 to a smaller diameter with the embolic debris 144 trapped inside the retracted embolic protection device 100.

In one particularly preferred embodiment, the embolic protection device 100 is configured to close the upstream end 108 of the cylindrical outer structure 102 first to assure that any captured emboli do not migrate out of the collection chamber 103. This can be accomplished by providing two separate pull loops 122 for selectively retracting the upstream and downstream retraction members 116, 120. Alternatively, it can be accomplished by configuring the connecting members 118 so that, when the pull loop 122 is pulled, the upstream retraction member 116 is automatically tightened before the downstream retraction member 120 is tightened.

The entire embolic protection device or a portion of it may be coated with an antithrombogenic coating, for example a bonded heparin coating, to reduce the formation of clots that could become potential emboli. Alternatively or in addition, the embolic protection device or a portion of it may have a drug-eluting coating containing an anti-inflammatory or anti-stenosis agent.

Figure 12:
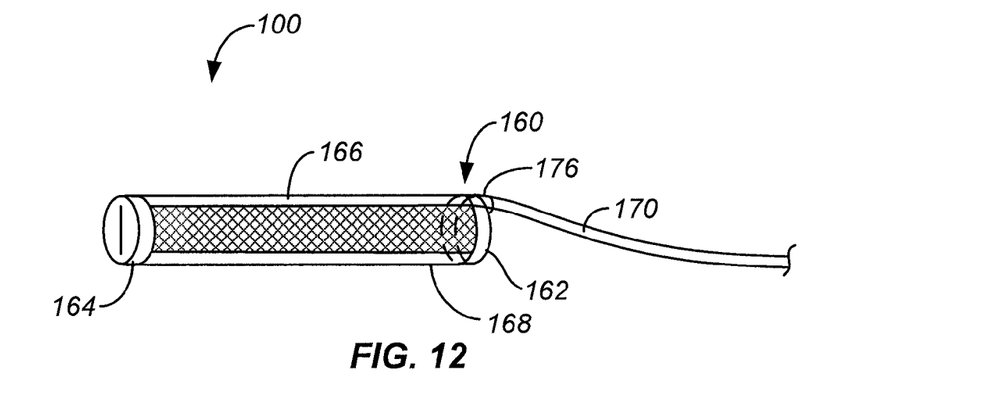
FIG. 12 shows an inflatable embodiment of an embolic protection device in an uninflated condition.

FIGS. 12 and 13 show an inflatable embodiment of the embolic protection device 100 of the present invention. FIG. 12 shows the embolic protection device 100 in an uninflated condition, and FIG. 13 shows the embolic protection device 100 in an inflated condition. The embolic protection device 100 is similar in structure to the embodiments previously described, with the notable difference that the filter mesh material is supported on an inflatable support framework 160. The inflatable support framework 160 includes a proximal inflatable toroidal balloon 162 and a distal inflatable toroidal balloon 164, and optionally includes one or more inflatable longitudinal struts 166, 168. The framework 160 may include one or more radial struts 172, 174 to support the narrow upstream end of the conical inner structure 104 where the catheter port 106 is located concentrically within the cylindrical outer structure 102. Optionally, the radial struts 172, 174 may also be inflatable. The inflatable support framework 160 may be constructed of a compliant, semicompliant or noncompliant polymer material or a combination thereof. An inflation tube 170 extends out of the patient's body for inflating and deflating the inflatable support framework 160 with a fluid medium, such as saline solution or carbon dioxide gas. Optionally, the inflation tube 170 may be detachable from the inflatable support framework 160 and a valve 176 may be provided for maintaining the framework 160 in an inflated condition once the inflation tube 170 has been detached.

The uninflated embolic protection device 100 may be delivered into the patient's aorta on a guidewire or delivery catheter and/or inside of a delivery sheath. Once, the embolic protection device 100 is in the proper position within the aortic arch, the inflatable support framework 160 is inflated through the inflation tube 170. At least the distal inflatable toroidal balloon 164, and optionally the proximal inflatable toroidal balloon 162, makes a seal with the aortic wall when inflated so that blood flow will be directed into the collection chamber 103 and through the filter mesh material to capture any potential emboli. If the embolic protection device 100 is intended for short term use, the proximal end of the inflation tube 170 may be left exposed at the insertion site. Alternatively, if the embolic protection device 100 is intended for long term use, the inflation tube 170 may be detached from the inflated embolic protection device 100. As another alternative, the proximal end of the inflation tube 170 may be buried under the patient's skin to allow later access for deflating and withdrawing the embolic protection device 100.

When the embolic protection device 100 is no longer needed, the inflatable support framework 160 is deflated and the embolic protection device 100 is withdrawn from the patient. Preferably, the embolic protection device 100 is configured such that the distal toroidal balloon 164 on the upstream end of the collection chamber 103 deflates first to effectively capture any potential emboli inside of the collection chamber 103. Other mechanisms described herein may also be used to assist in retracting the embolic protection device 100.

Other mechanisms may be employed for deploying and/or retrieving the embolic protection device 100. For example, the embolic protection device 100 can be elongated in the longitudinal direction to cause it contract radially. Releasing the tension on the embolic protection device 100 allows it to contract in the longitudinal direction and to expand radially for deployment. A retrieval catheter can be configured to apply longitudinal tension to the embolic protection device 100 to collapse it radially for withdrawal from the patient. Alternatively or in addition, the embolic protection device 100 can be twisted or wrapped to cause it contract radially. Releasing the embolic protection device 100 allows it to untwisted or unwrapped and to expand radially for deployment. A retrieval catheter can be configured to apply torque to the embolic protection device 100 to twist or wrap it to collapse it radially for withdrawal from the patient. These mechanisms may also be used in combination with the methods described above, such as those using retraction members or an inflatable support framework, to deploy and/or retrieve the embolic protection device 100.

Alternate embodiments of the embolic protection device 100 may combine features of the embodiments described herein to accomplish the same ends. For example, an embolic protection device 100 may be constructed with a single hoop 112 or inflatable toroidal balloon 164 on the upstream end of a cylindrical or conical outer structure 102 in contact with the vessel wall to anchor the device and to direct blood flow into the emboli collection chamber 103. The downstream end of the outer structure 102 may be constructed without a hoop or toroidal balloon, or alternatively with a smaller diameter hoop or toroidal balloon, as it is not critical for the downstream end of the embolic protection device 100 to contact or make a seal with the vessel wall. The inner conical structure 104 may be constructed with self-supporting filter mesh material or the filter mesh material may be supported on a framework of resilient struts and/or inflatable struts.

The embolic protection device of the present invention can also be used for embolic protection of other organ systems. For example, an embolic protection device can be deployed in the patient's descending aorta for preventing embolic particles in the aortic blood flow from entering the renal arteries and embolizing in the patient's kidneys.

While the present invention has been described herein with respect to the exemplary embodiments and the best mode for practicing the invention, it will be apparent to one of ordinary skill in the art that many modifications, improvements and subcombinations of the various embodiments, adaptations and variations can be made to the invention without departing from the spirit and scope thereof.

The invention claimed is:

1. An embolic protection device, comprising:
    an approximately cylindrical outer structure (102) made of a filter mesh material;
    an approximately conical inner structure (104) made of a filter mesh material positioned inside of the cylindrical outer structure (102);
    one or more radial support elements (174), each support element being connected at one end to a narrow upstream end of the conical inner structure (104) and at another end to the cylindrical outer structure (102) to maintain the narrow upstream end of the conical inner structure (104) within the cylindrical outer structure (102); and
    a graspable structure (122) configured to be engaged by a retrieval catheter;
    wherein on a downstream end (110) of the embolic protection device (100), a wider end of the conical inner structure (104) is joined to the cylindrical outer structure (102);
    wherein an upstream end (108) of the embolic protection device (100) is open for blood to flow between the conical inner structure (104) and the cylindrical outer structure (102);
    with a space between the conical inner structure (104) and the cylindrical outer structure (102) defining a collection chamber (103) for captured emboli;
    wherein the narrow upstream end of the conical inner structure (104) has a catheter port (106) configured for passage of a catheter shaft through the catheter port (106); and
    wherein the graspable structure (122) is disposed on the downstream end (110) of the embolic protection device (100).

2. The embolic protection device of claim 1, wherein the filter mesh material of the conical inner structure (104) and the cylindrical outer structure (102) is made from a fabric of knitted, woven or nonwoven fibers, filaments or wires and with a pore size chosen to prevent emboli over a predetermined size from passing through.

3. The embolic protection device of claim 1, wherein the filter mesh material of the conical inner structure (104) and the cylindrical outer structure (102) is made of a metal, a polymer or a combination thereof.

4. The embolic protection device of claim 1, wherein the filter mesh material of the conical inner structure (104) and the cylindrical outer structure (102) has an antithrombogenic coating on its surface.

5. The embolic protection device of claim 1, wherein the filter mesh material of the conical inner structure (104) and the cylindrical outer structure (102) has a pore size in the range of approximately 1 mm to 0.1 mm.

6. The embolic protection device of claim 1, wherein the catheter port (106) has a resilient seal configured for forming a seal around a catheter shaft placed through the catheter port (106).

7. The embolic protection device of claim 6, wherein the resilient seal has a closed position configured to form a seal to prevent passage of emboli over a predetermined size through the catheter port when there is not a catheter or other device present within the catheter port.

8. The embolic protection device of claim 1, wherein the embolic protection device (100) has an undeployed retracted condition and a deployed expanded condition.

9. The embolic protection device of claim 8, further comprising a delivery catheter (124) insertable through the catheter port (106) and configured to deliver the embolic protection device (100) into a blood vessel of a patient in the undeployed retracted condition.

10. The embolic protection device of claim 8, further comprising a tubular outer delivery sheath (130) to maintain the embolic protection device (100) in the undeployed retracted condition prior to deployment.

11. The embolic protection device of claim 8, wherein the filter mesh material of the conical inner structure (104) and the cylindrical outer structure (102) is a resilient material that can be compressed into the undeployed retracted condition and that will self-expand into the deployed expanded condition.

12. The embolic protection device of claim 1, wherein the filter mesh material of the conical inner structure (104) and the cylindrical outer structure (102) is supported by a framework that includes an upstream hoop (112), a downstream hoop (114) and at least one longitudinal strut (113) that form the cylindrical outer structure (102), and at least one angled strut (107) that, together with the downstream hoop (114), form the conical inner structure (104).

13. The embolic protection device of claim 12, wherein the framework is a self-expanding framework made of a resilient metal and/or polymer material.

14. The embolic protection device of claim 12, wherein the framework is made of a malleable or plastically deformable material.

15. The embolic protection device of claim 12, wherein the framework is made of a shape-memory material.

16. The embolic protection device of claim 1, wherein the filter mesh material of the conical inner structure (104) and the cylindrical outer structure (102) is supported by an inflatable support framework (160) that includes a proximal inflatable toroidal balloon (162), a distal inflatable toroidal balloon (164).

17. The embolic protection device of claim 1, wherein the conical inner structure (104) and the cylindrical outer structure (102) have approximately the same longitudinal dimensions.

18. The embolic protection device of claim 1, wherein the conical inner structure (104) is longer than the cylindrical outer structure (102) in a longitudinal direction.

19. The embolic protection device of claim 1, wherein the conical inner structure (104) is shorter than the cylindrical outer structure (102) in a longitudinal direction.

20. The embolic protection device of claim 1, further comprising at least one retraction member (116, 120) encircling the circumference of the cylindrical outer structure (102).

21. The embolic protection device of claim 20, wherein the graspable structure is connected to the retraction members (116, 120).

22. The embolic protection device of claim 6, wherein the resilient seal comprises an elastomeric disk (133) with a slit (134) through the elastomeric disk (133).

23. The embolic protection device of claim 6, wherein the resilient seal comprises an elastomeric disk (135) with a trap door flap (136) through the elastomeric disk (135) that can open by bending in an upstream direction to allow passage of a catheter.

24. The embolic protection device of claim 23, wherein the resilient seal comprises a second elastomeric disk (137) on a downstream side of the elastomeric disk (135) with a hole (138) through the second elastomeric disk (137) slightly smaller than the trap door flap (136).

25. The embolic protection device of claim 6, wherein the resilient seal comprises a plurality of resilient flaps (140), wherein the resilient flaps (140) overlap to form a seal when the resilient seal is in a closed position, and wherein the resilient flaps (140) are configured to bend back to allow passage of a catheter.

26. The embolic protection device of claim 1, wherein the embolic protection device (100) is retractable for retrieval from a patient's blood vessel.

27. The embolic protection device of claim 26, wherein the embolic protection device (100) is configured to retract an upstream end (108) of the cylindrical outer structure (102) first to assure that any captured emboli do not migrate out of the collection chamber (103) during retraction.

28. The embolic protection device of claim 1, wherein the open upstream end (108) is configured to seal against an aortic wall.

29. The embolic protection device of claim 1, wherein the device is configured to be self-supporting when deployed in an aorta.

30. The embolic protection device of claim 1, wherein the filter mesh material of the cylindrical outer structure (102) has a pore size which is the same as a pore size of the conical inner structure.

31. The embolic protection device of claim 1, wherein the one or more radial support elements comprise struts.

32. The embolic protection device of claim 1, wherein the struts are inflatable.

* * * * *